(12) United States Patent
Dziubak et al.

(10) Patent No.: US 10,980,411 B2
(45) Date of Patent: Apr. 20, 2021

(54) INFORMATION PROCESSING APPARATUS, INFORMATION PROCESSING METHOD, AND STORAGE MEDIUM

(71) Applicant: CANON KABUSHIKI KAISHA, Tokyo (JP)

(72) Inventors: Tomasz Dziubak, Toruń (PL); Tomasz Bajraszewski, Głogowo (PL); Sławomir Orłowski, Toruń (PL); Hiroshi Imamura, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 184 days.

(21) Appl. No.: 15/872,647

(22) Filed: Jan. 16, 2018

(65) Prior Publication Data
US 2018/0199806 A1 Jul. 19, 2018

(30) Foreign Application Priority Data
Jan. 18, 2017 (JP) .............................. JP2017-006977

(51) Int. Cl.
*G06K 9/00* (2006.01)
*A61B 3/00* (2006.01)
(Continued)

(52) U.S. Cl.
CPC ............ *A61B 3/0025* (2013.01); *A61B 3/102* (2013.01); *G06T 7/0012* (2013.01); *G06T 7/20* (2013.01); *G06T 7/73* (2017.01); *G06T 11/005* (2013.01); *G06T 2207/10101* (2013.01); *G06T 2207/30041* (2013.01); *G06T 2207/30101* (2013.01); *G06T 2210/41* (2013.01)

(58) Field of Classification Search
CPC ..... A61B 3/102; A61B 5/0066; A61B 3/0025; G06T 11/005; G06T 2207/10101; G06T 2207/30041; G06T 2207/30101; G06T 2210/41; G06T 7/0012; G06T 7/20; G06T 7/73
See application file for complete search history.

(56) References Cited

U.S. PATENT DOCUMENTS 8,857,988 B2 10/2014 Sharma et al.
2006/0119858 A1* 6/2006 Knighton ........... G01B 9/02091
356/479
(Continued)

FOREIGN PATENT DOCUMENTS

JP 2017221525 A 12/2017

*Primary Examiner* — Avinash Yentrapati
(74) *Attorney, Agent, or Firm* — Canon U.S.A., Inc. IP Division

(57) ABSTRACT

An information processing apparatus includes an acquisition unit configured to acquire a plurality of data sets each of which includes a plurality of pieces of tomographic data that represents a section of a fundus, the plurality of data sets not including the same tomographic data as each other, a first generation unit configured to generate at least one motion contrast image from each of the plurality of data sets acquired by the acquisition unit, without generating a motion contrast image from across the data sets acquired by the acquisition unit, and a second generation unit configured to generate a single motion contrast image representing a cross section at a predetermined position in the fundus, based on the motion contrast image generated from at least one of the plurality of data sets.

19 Claims, 8 Drawing Sheets

(51) Int. Cl.
*G06T 11/00* (2006.01)
*G06T 7/20* (2017.01)
*G06T 7/00* (2017.01)
*A61B 3/10* (2006.01)
*G06T 7/73* (2017.01)

(56) References Cited

U.S. PATENT DOCUMENTS

| | | | |
|---|---|---|---|
| 2012/0277579 A1* | 11/2012 | Sharma | A61B 3/102 |
| | | | 600/425 |
| 2013/0176532 A1* | 7/2013 | Sharma | A61B 3/102 |
| | | | 351/206 |
| 2014/0063460 A1* | 3/2014 | Borycki | G06T 7/337 |
| | | | 351/208 |
| 2015/0055089 A1* | 2/2015 | Aono | A61B 3/0025 |
| | | | 351/206 |
| 2015/0168127 A1* | 6/2015 | Takeno | A61B 5/0066 |
| | | | 356/479 |
| 2015/0374227 A1* | 12/2015 | Takeno | A61B 5/02 |
| | | | 600/425 |
| 2016/0040977 A1* | 2/2016 | An | A61B 3/102 |
| | | | 356/479 |
| 2016/0317016 A1* | 11/2016 | Oishi | A61B 3/102 |
| 2016/0371836 A1 | 12/2016 | Kuno et al. | |
| 2017/0258326 A1* | 9/2017 | Sakagawa | A61B 3/1025 |
| 2017/0360294 A1* | 12/2017 | Satake | A61B 3/1225 |
| 2018/0256024 A1* | 9/2018 | An | A61B 3/102 |
| 2019/0347797 A1* | 11/2019 | Bagherinia | G06T 5/50 |

* cited by examiner

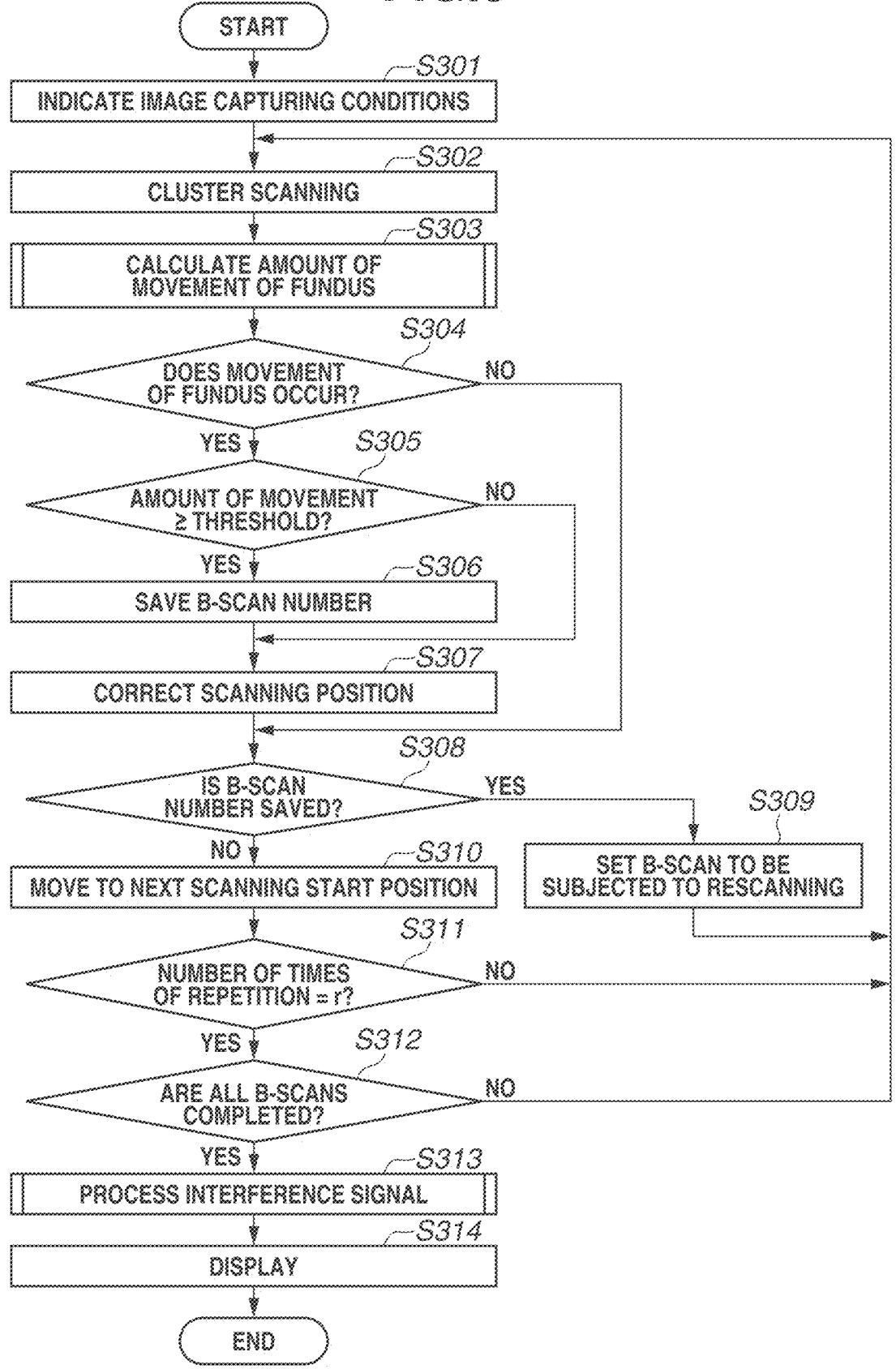

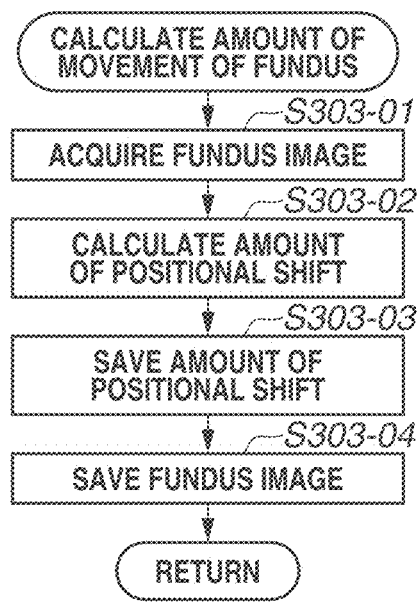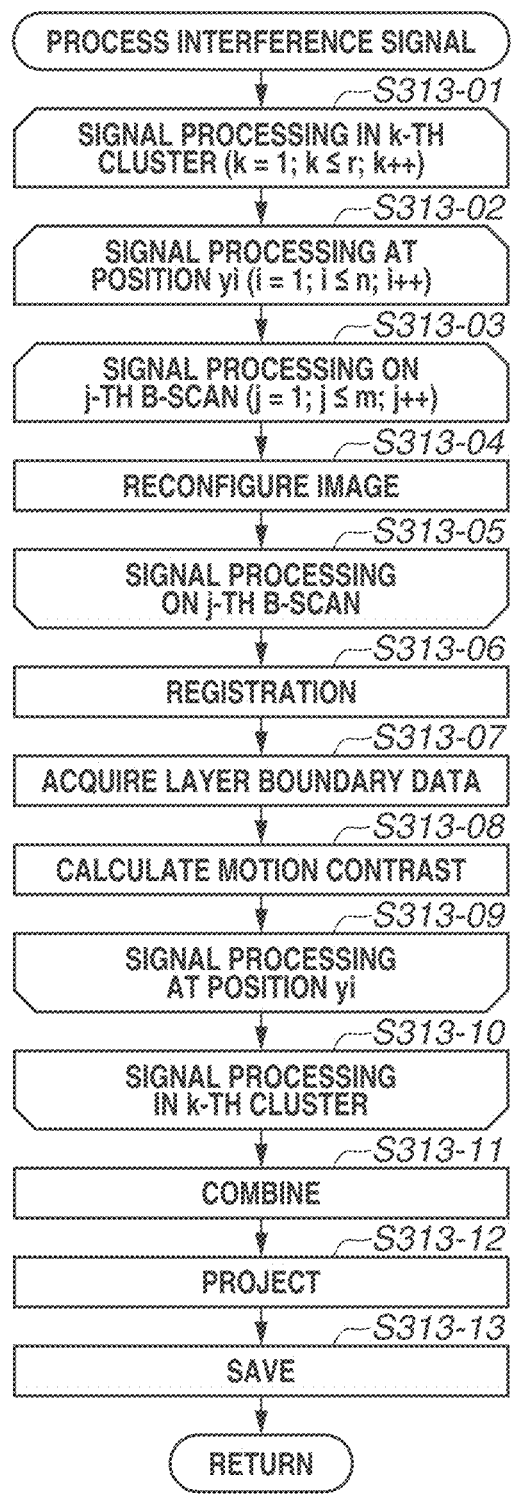

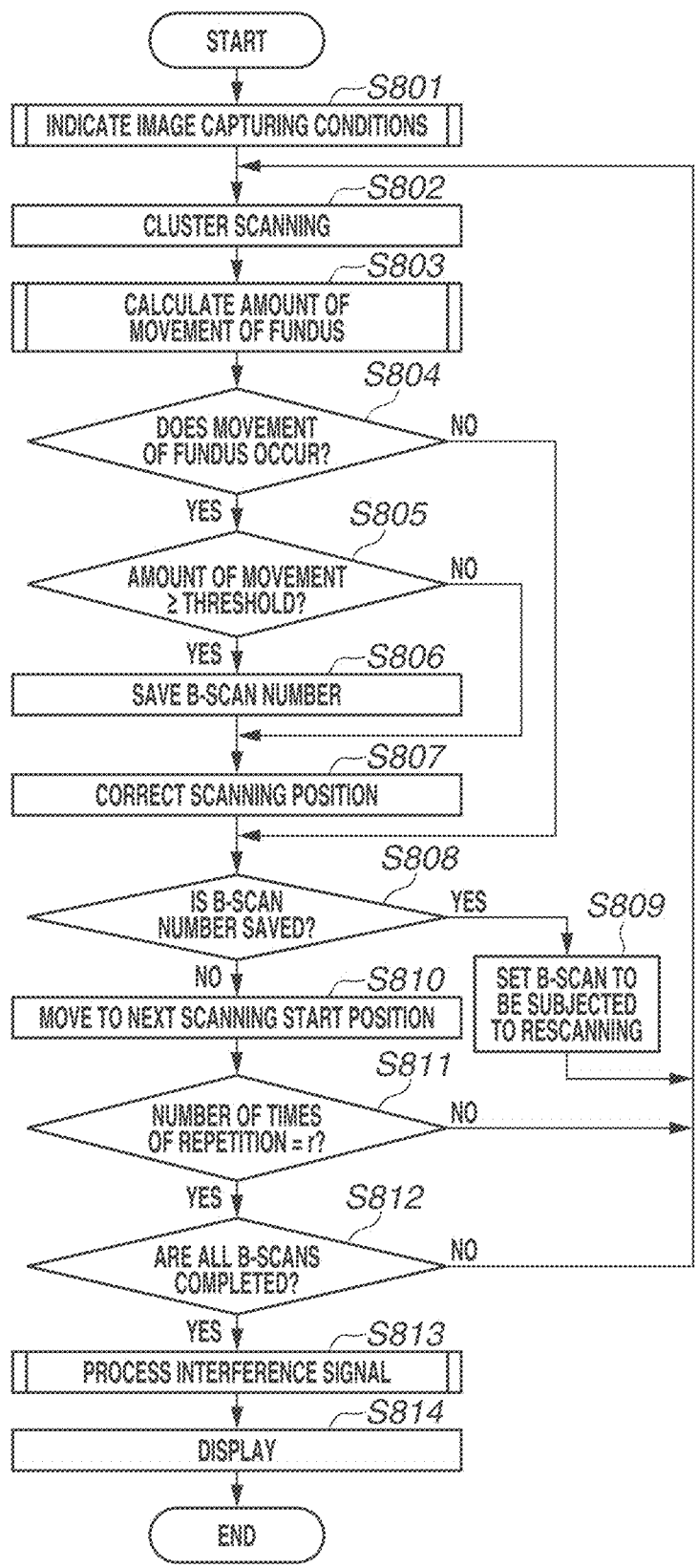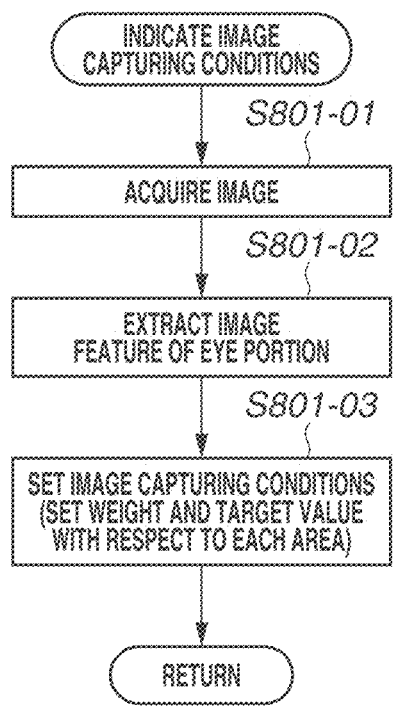

INFORMATION PROCESSING APPARATUS, INFORMATION PROCESSING METHOD, AND STORAGE MEDIUM

BACKGROUND

Field

The present invention relates to an information processing apparatus, an information processing method, and a storage medium.

Description of the Related Art

In ophthalmic practice, to grasp the condition of fundus blood vessels, optical coherence tomography angiography (hereinafter referred to as "OCTA") is increasingly used. The OCTA is for visualizing fundus blood vessels in three dimensions in a non-invasive manner using optical coherence tomography (OCT). In the OCTA, scanning is performed multiple times at the same position with measurement light, to obtain an OCTA image (also referred to as a "motion contrast image"). The process of performing scanning multiple times at the same position to obtain a motion contrast image is referred to as "cluster scanning", and a plurality of tomographic images obtained at the same position are referred to as a "cluster". It is known that if the number of tomographic images per cluster (the number of times of scanning at the same position) is increased, the contrast of the motion contrast image is enhanced.

The specification of U.S. Pat. No. 8,857,988 discusses an OCT device for discarding all clusters including tomographic images acquired during the period in which the motion of the subject's eye is detected, acquiring alternative clusters by performing rescanning, and then generating and displaying a motion contrast image.

SUMMARY

According to an aspect of the present invention, an information processing apparatus includes an acquisition unit configured to acquire a plurality of data sets each of which includes a plurality of pieces of tomographic data that represents a section of a fundus and is obtained based on measurement light controlled to perform scanning at the same position in the fundus in the same direction, the plurality of data sets not including the same tomographic data as each other, a first generation unit configured to generate at least one motion contrast image from each of the plurality of data sets acquired by the acquisition unit, without generating a motion contrast image from across the data sets acquired, by the acquisition unit, and a second generation unit configured to generate a single motion contrast image representing a cross section at a predetermined position in the fundus, based on the motion contrast image generated from at least one of the plurality of data sets.

Further features of the present invention will become apparent from the following description of exemplary embodiments with reference to the attached drawings.

BRIEF DESCRIPTION OF THE DRAWINGS

FIG. 3 is a flowchart illustrating an example of processing executed by an information processing system according to a first exemplary embodiment.

FIGS. 7A and 7B are flowcharts illustrating details of examples of processes executed in steps S303 and S313 according to the first exemplary embodiment.

FIG. 8A is a flowchart illustrating an example of processing executed by an information processing system according to a second exemplary embodiment, and FIG. 8B is a flowchart illustrating details of an example of a process executed, in step S801 according to the second exemplary embodiment.

DESCRIPTION OF THE EMBODIMENTS

If the number of tomographic images per cluster is increased to enhance the contrast of a motion contrast image, the image capturing time becomes long. Thus, it is highly likely that the state of a subject's eye is not stabilized, and rescanning is performed. Then, the acquisition of tomographic images for a single cluster by rescanning makes the image capturing time longer. As a result, it is difficult to acquire a motion contrast image.

The present invention is directed to stably acquiring a motion contrast image.

The present invention is not only directed to the above, but can also be directed to obtaining an operation and an effect that result from the configurations illustrated in the description of the embodiments below and cannot be obtained by a conventional technique.

The technique according to the disclosure will be described with reference to the attached drawings. The configurations illustrated in the following exemplary embodiments are merely illustrative, and the present invention is not limited to the illustrated configurations. Each of the embodiments of the present invention described below can be implemented solely or as a combination of a plurality of the embodiments or features thereof where necessary or where the combination of elements or features from individual embodiments in a single embodiment is beneficial.

With reference to the drawings, an information processing system including an information processing apparatus according to a first exemplary embodiment is described below.

Figure 2A:
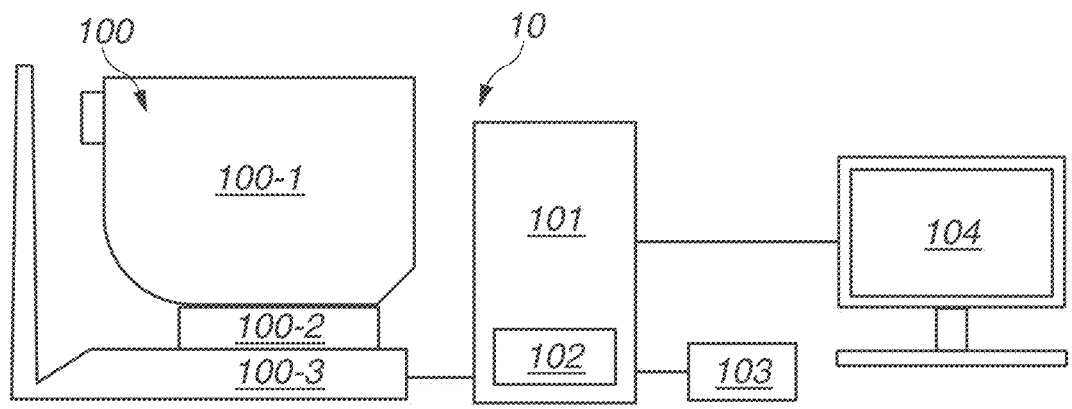
FIG. 2A is a diagram illustrating an example of an information processing system according to the present exemplary embodiment.

FIG. 2A is a diagram illustrating an example of the configuration of an information processing system 10 including an information processing apparatus 101 according to the present exemplary embodiment. As illustrated in FIG. 2A, the information processing system 10 includes an optical coherence tomography (OCT) device 100, an information processing apparatus 101, a storage unit 102, an input unit 103, and a display unit 104. Although the OCT device 100, the information processing apparatus 101, the input unit 103, and the display unit 104 are separate components in the example of FIG. 2A, at least some of these components may be configured in an integrated manner. Further, the storage unit 102 may be provided outside the information processing apparatus 101.

The information processing apparatus 101 is connected to the OCT device 100 (also referred to as "OCT"), the storage unit 102, the input unit 103, and the display unit 104 via interfaces so that the information processing apparatus 101 can communicate with these components.

The OCT device 100 is a device for capturing a tomographic image of the eye portion by irradiating an eye portion with measurement light. In the present exemplary embodiment, as the OCT device 100, spectral domain OCT (SD-OCT) is used. The present invention is not limited to this. Alternatively, for example, the OCT device 100 may be configured using swept-source OCT (SS-OCT). The OCT device 100 may use any method so long as the device can capture a tomographic image of an eye portion.

In FIG. 2A, the OCT device 100 includes a measurement optical system 100-1, a stage unit 100-2, and a base unit 100-3. The measurement optical system 100-1 is an optical system for acquiring an anterior eye portion image, a scanning laser ophthalmoscopy (SLO) fundus image of a subject's eye, and a tomographic image. The stage unit 100-2 enables the measurement optical system 100-1 to move right and left and backwards and forwards. A spectrometer is built into the base unit 100-3. Alternatively, the spectrometer may be built into a component other than the base unit 100-3.

The information processing apparatus 101 is a computer for controlling the stage unit 100-2, controlling an alignment operation, and reconfiguring a tomographic image.

The storage unit 102 stores a program for capturing a tomographic image, and the statistics of a normal eye database. Further, the storage unit 102 stores information regarding a subject's eye, captured image data, image capturing parameters, and parameters set by an operator in association with each other. The information regarding a subject's eye is information of at least one of, for example, the name, the age, and the gender of a patient. Further, the image data is data of at least one of a tomographic image, an SLO fundus image, and an optical coherence tomography angiography (OCTA) image. The storage unit 102 at least needs to be able to store data and is any type of medium, such as a hard disk drive (HDD), a solid-state drive (SSD), a random-access memory (RAM), or a read-only memory (ROM). Further, the storage unit 102 may include a plurality of types of media.

The input unit 103 gives an instruction to the computer. Specifically, the input unit 103 includes at least one of a keyboard and a mouse.

The display unit 104 is composed of a monitor, for example. The input unit 103 may be a touch panel. In this case, the input unit 103 and the display unit 104 are configured in an integrated manner.

(Configuration of OCT Device)

Figure 2B:
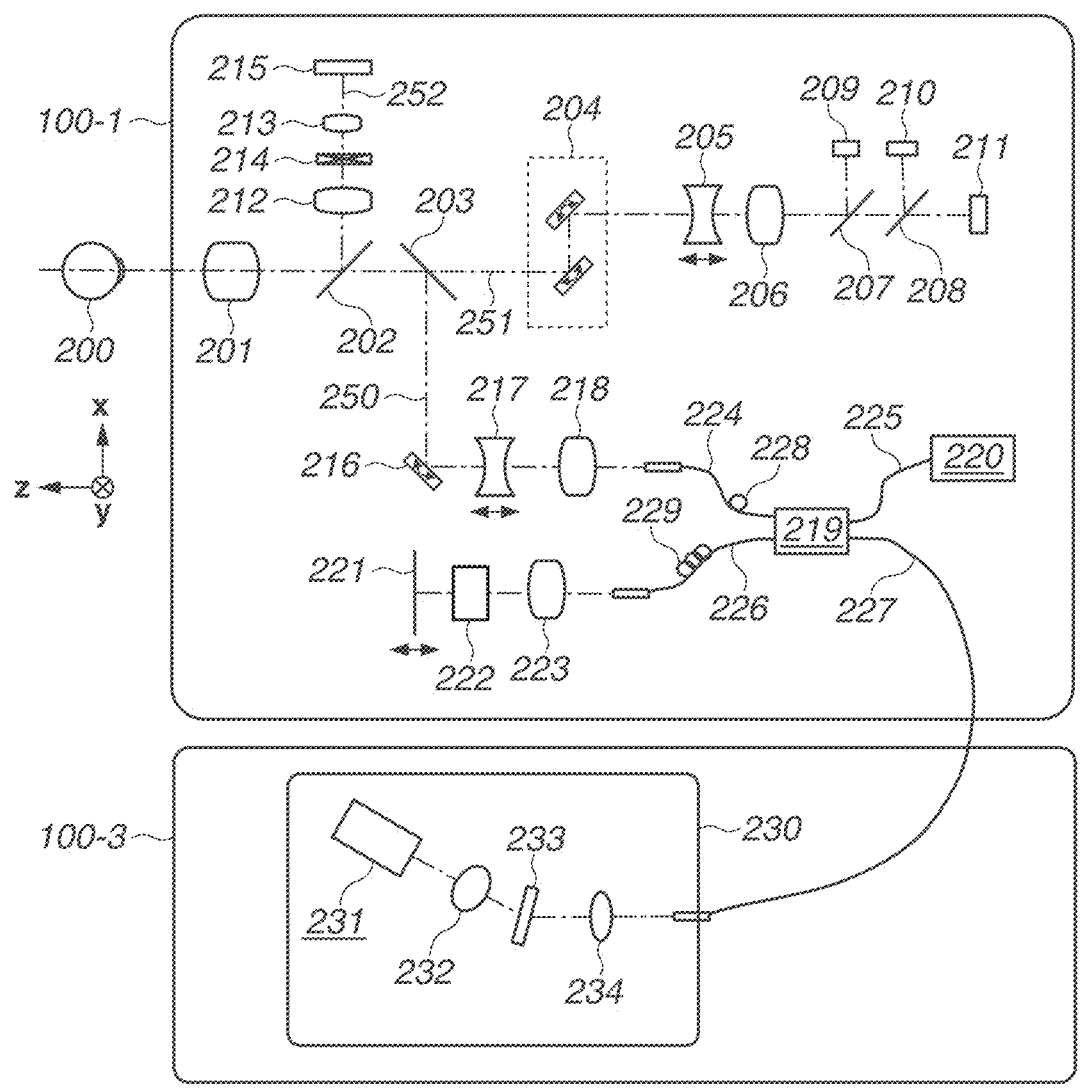
FIG. 2B is a diagram illustrating an example of a measurement optical system included in a tomographic image capturing device forming the information processing system.

With reference to FIG. 2B, examples of the configurations of the measurement optical system and the spectrometer in the OCT device 100 according to the present exemplary embodiment are described.

First, the measurement optical system 100-1 is described. An objective lens 201 is installed to be opposed to a subject's eye 200, and a first dichroic mirror 202 and a second dichroic mirror 203 are placed on the optical axis of the objective lens 201. The dichroic mirrors 202 and 203 branch an optical path based on wavelength bands into an optical path 250 for an OCT optical system, an optical path 251 for an SLO optical system and a fixation lamp, and an optical path 252 for observing the anterior eye.

The optical path 251 for the SLO optical system and the fixation lamp includes an SLO scanning unit 204, lenses 205 and 206, a mirror 207, a third dichroic mirror 208, an avalanche photodiode (APD) 209, an SLO light source 210, and a fixation lamp 211.

The mirror 207 is a prism on which a perforated mirror or a hollow mirror is vapor-deposited. The mirror 207 separates illuminating light from the SLO light source 210 and returning light from the subject's eye 200. The third dichroic mirror 208 separates the optical path 251 based on wavelength bands into an optical path for the SLO light source 210 and an optical path for the fixation lamp 211.

The SLO scanning unit 204 scans the subject's eye 200 with light emitted from the SLO light source 210. The SLO scanning unit 204 includes an X-scanner for performing scanning in an X-direction, and a Y-scanner for performing scanning in a Y-direction. In the present exemplary embodiment, for example, the X-scanner needs to perform high-speed scanning and therefore includes a polygon mirror. The Y-scanner includes a galvanometer mirror.

The lens 205 is driven by a motor (not illustrated) to bring the SLO optical system and the fixation lamp 211 into focus. The SLO light source 210 generates light of a wavelength near 780 nm, for example. The numerical value of the wavelength is illustrative, and may be another value. The APD 209 detects returning light from the subject's eye 200. The fixation lamp 211 generates visible light to urge the subject to perform fixation.

Light emitted from the SLO light source 210 is reflected from the third dichroic mirror 208, passes through the mirror 207 and the lenses 206 and 205, and is scanned over the subject's eye 200 by the SLO scanning unit 204. Returning light from the subject's eye 200 returns along the same path as that of the illuminating light, is then reflected from the mirror 207, and is guided to the APD 209. Based on the output of the APD 209, an SLO fundus image is obtained.

Light emitted from the fixation lamp 211 passes through the third dichroic mirror 208, the mirror 207, and the lenses 206 and 205 and forms a predetermined shape at any positron on the subject's eye 200 by the SLO scanning unit 204, so that the subject is urged to perform fixation.

On the optical path 252 for observing the anterior eye, lenses 212 and 213, a split prism 214, and a charge-coupled device (CCD) 215 for observing an anterior eye portion and detecting infrared light are placed. The CCD 215 has sensitivity near the wavelength of irradiation light (not illustrated) for observing the anterior eye portion, specifically near 970 nm. The split prism 214 is placed at a position conjugate to the pupil of the subject's eye 200 and can detect the distance in a Z-axis direction (the optical axis direction) from the measurement optical system 100-1 to the subject's eye 200 as the degree of shift of a split image of the anterior eye portion. The method for detecting the distance in the Z-axis direction using the split image is known, and therefore is not described in detail here.

As described above, the optical path 250 for the OCT optical system forms an OCT optical system and is used to capture a tomographic image of the subject's eye 200. More specifically, the optical path 250 for the OCT optical system is used to obtain an interference signal for forming a tomographic image. An XY-scanner 216 is used to scan the subject's eye 200 with light. Although illustrated as a single mirror in FIG. 2B, actually, the XY-scanner 216 includes two galvanometer mirrors for performing scanning in two axial directions, namely the X-axis and Y-axis directions.

Between lenses 217 and 218, the lens 217 is driven by a motor (not illustrated) to focus light from an OCT light source 220, which is emitted from a fiber 224 connected to an optical coupler 219, on the subject's eye 200. By this focusing, returning light from the subject's eye 200 forms a spot-like image and is incident on the extremity of the fiber 224. Next, the configurations of an optical path from the OCT light source 220, a reference optical system, and the spectrometer are described. FIG. 2B illustrates an OCT light source 220, a reference mirror 221, dispersion compensation glass 222, a lens 223, an optical coupler 219, and single-mode optical fibers 224 to 227, which are connected to the optical coupler 219 in an integrated manner, and a spectrometer 230.

These components form a Michelson interferometer. Light emitted from the OCT light source 220 passes through the optical fiber 225 and is divided by the optical coupler 219 into measurement light on the optical fiber 224 side and reference light on the optical fiber 226 side. The measurement light passes through the optical path for the OCT optical system and irradiates the subject's eye 200 to be observed. Then, returning light from the subject's eye 200 is reflected and scattered by the subject's eye 200 and reaches the optical coupler 219 through the same optical path as that of the measurement light proceeding to the eye.

On the other hand, the reference light passes through the optical fiber 226, the lens 223, and the dispersion compensation glass 222. Then, the reference light reaches and is reflected from, the reference mirror 221. Then, the reference light returns along the same optical path and reaches the optical coupler 219. At this time, the dispersion compensation glass 222 is a dispersion compensation member inserted to balance the wavelength dispersion of the measurement light with the wavelength dispersion of the reference light.

The optical coupler 219 multiplexes the measurement light and the reference light to obtain interference light.

At this time, when the optical path length of the measurement light and the optical path length of the reference light become almost the same, interference occurs. The reference mirror 221 is held so that the reference mirror 221 can be adjusted in the optical axis direction by a motor and a driving mechanism (not illustrated). Thus, the match the optical path length of the reference light to the optical path length of the measurement light. The interference light is guided to the spectrometer 230 through the optical fiber 227.

Further, polarization adjustment units 228 and 229 are provided in the optical fibers 224 and 226, respectively, and adjust the polarization of light. Each of the polarization adjustment units 228 and 229 includes some portions where the optical fiber is drawn into a loop. These loop-like portions are rotated about the longitudinal direction of the fiber so that the fiber is twisted. Thus, it is possible to adjust and match the polarization states of the measurement light and the reference light.

The spectrometer 230 includes lenses 232 and 234, a diffraction grating 233, and a line sensor 231. The interference light emitted from the optical fiber 227 becomes parallel light through the lens 234 and is then dispersed by the diffraction grating 233. Then, the dispersed light forms an image on the line sensor 231 by the lens 232.

Next, the periphery of the OCT light source 220 is described. The OCT light source 220 is a superluminescent diode (SLD), which is a typical low-coherence light source. For example, the OCT light source 220 has a center wavelength of 855 nm and a wavelength bandwidth of about 100 nm. The numerical values of the wavelengths are illustrative, and may be other numerical values.

Although an SLD is selected as the type of the light source, the OCT light source 220 at least needs to be able to emit low-coherence light, and therefore may use amplified spontaneous emission (ASE). Considering the measurement of the eye, near-infrared light is appropriate for the center wavelength. Further, the center wavelength influences the horizontal resolution of a tomographic image to be obtained. Thus, it is desirable that the center wavelength should be as short as possible. For both reasons, the center wavelength is set to 855 nm. The value of the wavelength may be another value.

In the present exemplary embodiment, a Michelson interferometer is used as the interferometer. Alternatively, a Mach-Zehnder interferometer may be used. It is desirable to use a Mach-Zehnder interferometer in a case where the difference in amount of light between the measurement light and the reference light is great, and use a Michelson interferometer in a case where the difference in amount of light between the measurement light and the reference light is relatively small.

(Configuration of Information Processing Apparatus)

Figure 1:
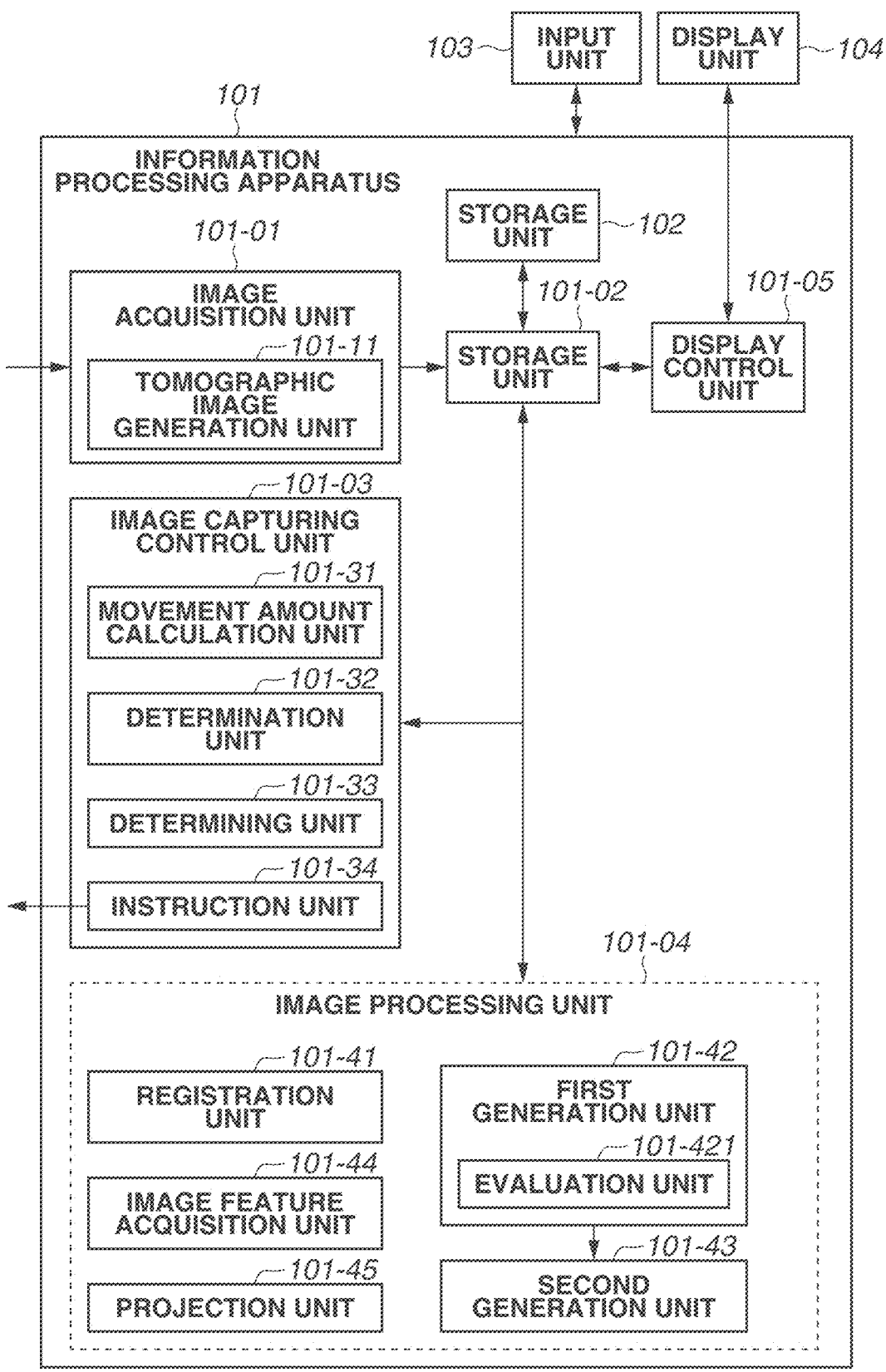
FIG. 1 is a block diagram illustrating an example of a configuration of an information processing apparatus according to the present exemplary embodiment.

With reference to FIG. 1, an example of the configuration of the information processing apparatus 101 according to the present exemplary embodiment is described.

The information processing apparatus 101 includes a central processing unit (CPU) (not illustrated) and a storage unit 101-02. The storage unit 101-02 and the CPU are connected together so that the storage unit 101-02 and the CPU can communicate with each other. The CPU executes a program stored in the storage unit 101-02, to function as an image acquisition unit 101-01, an image capturing control unit 101-03, an image processing unit 101-04, and a display control unit 101-05.

The information processing apparatus 101 may include a single CPU and a single storage unit 101-02, or may include a plurality of CPUs and a plurality of storage units 101-02. Further, a processing device is not limited to a CPU, and may be a processor, such as a graphics processing unit (GPU), an application-specific integrated circuit (ASIC), a microprocessor unit (MPU), or a field-programmable gate array (FPGA). That is, at least one or more processors (hardware processors) and at least one memory are connected together, and in a case where the at least one or more processors execute a program stored in the at least one memory, the information processing apparatus 101 functions as the above components. Further, the information processing apparatus 101 may include a plurality of types of processors. For example, the image processing unit 101-04 may be achieved by dedicated hardware, such as an ASIC, and the display control unit 101-05 may be achieved by a GPU.

The image acquisition unit 101-01 acquires signal data (interference signal data) of a tomographic image captured by the OCT device 100. In a case where measurement light is controlled to perform scanning multiple times at the same position in the fundus in the same direction to acquire a motion contrast image, the image acquisition unit 101-01 acquires a data set (a cluster) including a plurality of pieces of tomographic data representing a section of the fundus. Further, in a case where there are a plurality of such data sets, the image acquisition unit 101-01 corresponds to an example of an acquisition unit configured to acquire a plurality of data sets that include a plurality of pieces of tomographic data representing a section of a fundus and obtained based on measurement, light controlled to perform scanning at the same position in the fundus in the same direction, and do not include the same tomographic data as each other.

In the present exemplary embodiment, for example, each of the plurality of pieces of tomographic data included in the plurality of clusters (data sets) is tomographic data representing a section of the fundus and obtained based on the measurement, light controlled to perform scanning at the same position in the fundus.

Further, the image acquisition unit 101-01 includes a tomographic image generation unit 101-11. The tomographic image generation unit 101-11 performs signal processing on the acquired signal data of the tomographic image to generate a tomographic image and stores the generated tomographic image in the storage unit 101-02. Data including at least one of the tomographic image and the signal data will occasionally be referred to collectively as "tomographic data". Further, the image acquisition unit 101-01 may acquire signal data of an SLO fundus image and generate an SLO fundus image.

The storage unit 101-02 stores various types of data. The storage unit 101-02 at least needs to be able to store data and is any type of medium, such as an HDD, an SSD, a RAM, or a ROM, Further, the storage unit 101-02 may include a plurality of types of media.

The image capturing control unit 101-03 controls the image capturing of the subject's eye 200 by the OCT device 100. The image capturing control unit 101-03 includes a movement amount calculation unit 101-31, a determination unit 101-32, a determining unit 101-33, and an instruction unit 101-34.

The movement amount, calculation unit 101-31 calculates the amount of movement of the subject's eye 200. For example, the movement amount calculation unit 101-31 compares a plurality of temporally consecutive SLO fundus images acquired by the OCT device 100 to calculate the amount of movement of the subject's eye 200.

The determination unit 101-32 determines whether the capturing of an image is failed, or determines whether it is necessary to recapture an image (perform rescanning). The determination unit 101-32 corresponds to an example of a determination unit configured to determine tomographic data that requires rescanning. For example, based on the amount of movement of the subject's eye 200 calculated by the movement amount calculation unit 101-31, the determination unit 101-32 determines whether it is necessary to recapture an image (perform rescanning).

The determining unit 101-33 determines a cluster including a tomographic image of which the capturing is failed. The determining unit 101-33 corresponds to an example of a determining unit configured to determine, among the plurality of data sets, a data set including the tomographic data that requires rescanning according to the determination by the determination unit. Further, the determining unit 101-33 corresponds to an example of a determining unit configured to determine a data set including the tomographic data of which the acquisition is failed according to the determination by the determination unit.

The instruction unit 101-34 indicates image capturing parameters regarding the normal capturing of an image or the recapturing of an image to the OCT device 100.

Based on a plurality of tomographic images acquired by the image acquisition unit 101-01, the image processing unit 101-04 generates a motion contrast image.

The image processing unit 101-04 includes a registration unit 101-41, a first generation unit 101-42, a second generation unit 101-43, an image feature acquisition unit 101-44, and a projection unit 101-45.

The registration unit 101-41 performs registration between the plurality of tomographic images. As the technique for the registration, various known techniques can be used. For example, the registration unit 101-41 performs registration between the plurality of tomographic images to maximize the correlations between the plurality of tomographic images.

The first generation unit 101-42 generates at least one motion contrast image with respect to each cluster (data set). That is, the first generation unit 101-42 corresponds to an example of a first generation unit configured to generate a motion contrast image from across data sets acquired by the acquisition unit, without generating a motion contrast image from across the data sets acquired by the acquisition unit.

Further, the first generation unit 101-42 includes an evaluation unit 101-421.

The evaluation unit 101-421 determines whether the cluster includes tomographic data inappropriate for calculating motion contrast. That is, the evaluation unit 101-421 determines tomographic data inappropriate for generating the motion contrast image.

Based on the motion contrast image generated by the first generation unit 101-42, the second generation unit 101-43 generates a single motion contrast image representing a cross section at a predetermined position in the fundus. For example, the second generation unit 101-43 combines the motion contrast images obtained from all the plurality of data sets to generate the single motion contrast image representing the cross section at the predetermined position in the fundus. That is, the second generation unit 101-43 combines the plurality of motion contrast images obtained from the plurality of respective data sets to generate the single motion contrast image representing the cross section at the predetermined position in the fundus. The process of combining the motion contrast images includes, for example, an addition process and an averaging process.

For example, in a case where motion contrast images are obtained from only some of the plurality of data sets, then based on the obtained motion contrast images, the second generation unit 101-43 may generate the single motion contrast image representing the cross section at the predetermined position in the fundus. That is, the second generation unit 101-43 corresponds to an example of a second generation unit configured to, based on the motion contrast image generated from at least one of the plurality of data sets, generate a single motion contrast image representing a cross section at a predetermined position in the fundus.

For example, in a case where tomographic images in some of a plurality of certain clusters are discarded, the second generation unit 101-43 may generate, without performing rescanning, the single motion contrast image representing the cross section at the predetermined position in the fundus from at least one or more motion contrast images obtained from the remaining clusters from which tomographic images are not discarded. That is, based on a motion contrast image obtained from, among the plurality of data sets, a data set other than the data set determined by the determining unit, the second generation unit 101-43 generates the single motion contrast image representing the cross section at the predetermined position in the fundus. A user may be able to change whether to perform rescanning.

The image feature acquisition unit 101-44 acquires an image feature included in a tomographic image. For example, the image feature acquisition unit 101-44 acquires a layer boundary from a tomographic image. As the method for acquiring the layer boundary, various known methods can be used. For example, the image feature acquisition unit 101-44 can identify as the layer boundary a portion in which a change in the luminance in the depth direction is equal to or greater than a predetermined value. The image feature acquisition unit 101-44 may acquire a layer boundary from a single tomographic image included in a cluster, or may acquire a layer boundary from an averaged image obtained by averaging a plurality of tomographic images included in a cluster.

The projection unit 101-45 projects in the depth direction a motion contrast value in a projection range determined based on the acquired layer boundary to generate a two-dimensional motion contrast image (a motion contrast en-face image). At this time, the "motion contrast value" refers to, for example, the value of each pixel included in the motion contrast image.

In the present exemplary embodiment, a case is described where the determination unit 101-32 and the determining unit 101-33 are included in the image capturing control unit 101-03. The present invention, however, is not limited to this. Alternatively, the configuration may be such that the determination unit 101-32 and the determining unit 101-33 are included in the image processing unit 101-04. That is, the functions of the information processing apparatus 101 illustrated in FIG. 1 at least need to be included in the information processing apparatus 101. Yet alternatively, another information processing apparatus may be put in charge of some of the functions.

(Operation of Information Processing Apparatus)

Next, with reference to FIG. 3, an example of the processing procedure of the information processing apparatus 101 according to the present exemplary embodiment is illustrated. FIG. 3 is a flowchart illustrating the flow of the operation processing of the entirety of the system according to the present exemplary embodiment.

<Step S301>

An operator operates the input unit 103 to set image capturing conditions for capturing a motion contrast image for the image capturing control unit 101-03 of the information processing apparatus 101 and instruct the image capturing control unit 101-03 to start capturing images. The image capturing control unit 101-03 receives the image capturing conditions and the instruction from the operator through the input unit 103.

In the present exemplary embodiment, the operator indicates the following parameters as the image capturing conditions. That is, the operator indicates the fixation position, the number of A-scans (p) per B-scan, the number of samplings (n) in a sub-scanning direction, the number of B-scans (m) per cluster, the number of clusters (r) at approximately the same position in the sub-scanning direction, the distance ($\Delta x$) between A-scans, and the distance ($\Delta y$) between B-scans. The operator does not need to input all the above parameters, and may input only some of the above parameters. Further, the operator may indicate not only the above parameters but also any known image capturing parameter. For example, the operator may indicate the image capturing position in the fundus or the image capturing angle of view as a parameter.

Figure 5A:
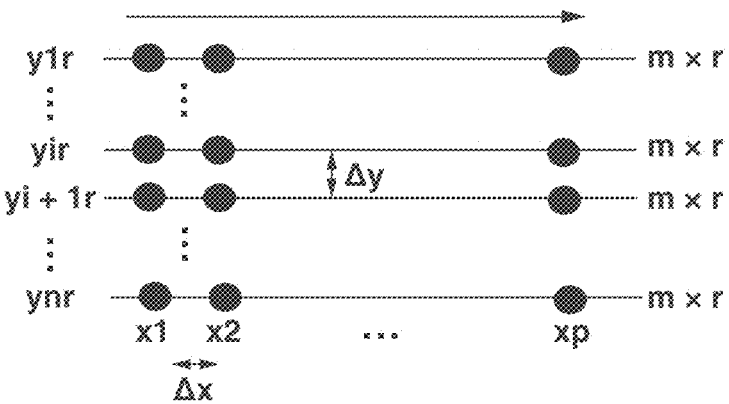
FIGS. 5A, 5B, and 5C are diagrams illustrating examples of processing executed in steps S302 and S310 according to the first exemplary embodiment.

With reference to FIG. 5A, the above image capturing conditions are described. OCTA measures changes over time in an OCT interference signal due to the movement of erythrocytes in blood vessels and therefore needs to perform scanning multiple times at the same position in the fundus. However, the subject's eye moves, and therefore, even if an attempt is made to perform scanning at the same position in the fundus, scanning may not always be able to be performed at the same position in the fundus. Further, also in a case where an OCT device has a tracking function for tracking a subject's eye, scanning may not always be able to be performed at the same position in the fundus due to the imperfection of the tracking function. That is, even if a device uses measurement light controlled to perform scanning at the same position in the fundus, the device cannot always perform scanning at exactly the same position in the fundus. Thus, in the specification, the same position in the fundus is a concept including not only exactly the same position in the fundus but also approximately the same position in the fundus.

If the number of times m of scanning at the same position in the fundus is set to be great, the number of signals obtained at the same position increases. Thus, the detection accuracy of bloodstream is improved. Meanwhile, the scanning time becomes long, and rescanning frequently occurs due to involuntary eye movement during scanning. This increases the burden on the subject.

In the present exemplary embodiment, instead of setting the number of times m of scanning per cluster to be great and performing cluster scanning; once, the number of times of scanning per cluster is set to be small, and cluster scanning is executed multiple times (r). Then, the second generation unit 101-43 combines motion contrast images obtained at each time of cluster scanning, so that a high-contrast OCTA image is acquired. In the present exemplary embodiment, the number of times m of scanning per cluster is set to m=3. Alternatively, m may be any value such as 2 or 4 or more. For example, m may be changed to any natural number according to the A-scan speed or the amount of movement of the subject's eye 200. That is, in the present exemplary embodiment, the numbers of pieces of tomographic data included in the plurality of data sets are equal to each other. For example, the numbers of pieces of tomographic data included in the plurality of data sets are two or three. The numbers of pieces of tomographic data included in the plurality of data sets do not necessarily need to be equal to each other.

In FIG. 5A, p indicates the number of A-scans in a single B-scan, and n indicates the maximum value of a position (Yi) in the sub-scanning direction. That is, a planar surface image size is determined by p×n. If p×n is great, an image can be captured at a wide angle of view so long as the same measurement pitch is set. However, the scanning time becomes long, and the burden on the subject increases as described above.

In FIG. 5A, $\Delta x$ indicates the distance (an x-pitch) between x-positions adjacent to each other, and $\Delta y$ is the distance (a y-pitch) between y-positions adjacent to each other. In the present exemplary embodiment, the x-pitch is determined as ½ of the beam spot diameter of irradiation light on the fundus and is 10 μm. Further, similarly to $\Delta x$, $\Delta y$ is also 10 μm. The values of the pitches are not limited to these examples, and the x-pitch and the y-pitch may be changed to any values. Regarding the x-pitch and the y-pitch, if the beam spot diameter is made great, the definition decreases, but a wide-range image can be acquired with small data capacity.

As is clear from FIG. 5A, to acquire a plurality of data sets, measurement light is controlled to perform scanning at the same position in the fundus in the same direction (the horizontal direction).

The image capturing control unit 101-03 controls the OCT device 100 to perform cluster scanning based on the image capturing conditions indicated in step S301. That is, the image capturing control unit 101-03 controls the OCT device 100 to repeat B-scans m times at the same; position in the fundus. Based on this control, the OCT device 100 repeats B-scans m times at the same position in the fundus. That is, the OCT device 100 executes cluster scanning.
<Step S303>

The movement amount calculation unit 101-31 performs registration between frames temporally adjacent to each other in an SLO fundus image (a moving image) to calculate the amount of movement of the fundus of the subject's eye 200. Further, the movement amount calculation unit 101-31 stores the calculated amount of movement in the storage unit 101-02.

The acquisition time of a single 310 fundus image in the present exemplary embodiment is about 30 milliseconds, for example. In the present exemplary embodiment, the calculation, time required to calculate the amount of movement of the fundus is sufficiently shorter than 30 milliseconds. Thus, it may be considered that the amount of movement of the fundus is calculated every 30 milliseconds. Meanwhile, the time required to capture a B-scan depends on the time required per A-scan and the number of A-scans. In the present exemplary embodiment, for example, the time required per A-scan is about 10 microseconds, and a 3-scan image includes 1000 A-scans. Thus, the time required to capture a B-scan is about 10 milliseconds. Thus, in the present exemplary embodiment, while the amount of movement of the fundus is calculated once from an SLO fundus image, 3-scans are executed, about, three times. The above numerical values are illustrative, and may be other numerical values.

With reference to a flowchart illustrated in FIG. 7A, a description is given of the details of the process of calculating the amount of movement of the fundus (the amount of shift in the measurement light irradiation position caused by the motion of the subject's eye 200) executed in step S303. FIG. 7A is a diagram illustrating an example of the flow of the calculation of the amount of movement of the fundus in fundus tracking.
<Step S303-01>

The image acquisition unit 101-01 acquires a two-dimensional image of the fundus of the subject's eye 200. Specifically, based on returning light obtained by scanning the fundus using the X-scanning scanner and the Y-scanning scanner included in the SLO scanning unit 204, the image acquisition unit 101-01 acquires an SLO fundus image. The SLO fundus image acquired by the image acquisition unit 101-01 is a moving image, for example. That is, the image acquisition unit 101-01 sequentially acquires SLO fundus images.
<Step S303-02>

The movement amount calculation unit 101-31 calculates the amount of movement using two fundus images, namely the previous SLO fundus image saved in the storage unit 101-02 and the current SLO fundus image. Specifically, the movement amount calculation unit 101-31 detects the amount of displacement in two dimensions (the X- and Y-directions) in a region of interest on the images to calculate the amount of movement of the fundus. Further, the movement amount calculation unit 101-31 may not only calculate the displacement in the X- and Y-directions, but also calculate the amount of change in the angle in a rotational direction and include the amount of change in the amount of movement.
<Step S303-03>

The image capturing control unit 101-03 stores the calculated amount of movement of the fundus in the storage unit 101-02 so that the amount of movement of the fundus is used by the information processing apparatus 101 to correct the scanning position or perform rescanning.
<Step S303-04>

The image capturing control unit 101-03 stores the acquired fundus image in the storage unit 101-02 so that the fundus image is used to calculate the amount of movement next. Step S303-04 may be performed simultaneously with step S303-01.

As described above, every time the SLO scanning unit 204 two-dimensionally scans the fundus, the image capturing control unit 101-03 calculates the amount of movement of the fundus according to the above flow.
<Step S304>

Referring back to FIG. 3, in step S304, the determination unit 101-32 determines whether the movement of the fundus occurs during scanning with measurement light. In the present exemplary embodiment, for example, if the determination unit 101-32 succeeds in reading from the storage unit 101-02 the amount of positional shift calculated and saved in step S303, the determination unit 101-32 determines that the movement of the fundus occurs. Further, if the amount of positional shift is not saved in the storage unit 101-02, the determination unit 101-32 determines that the movement of the fundus does not occur. In a case where the movement of the fundus occurs (YES in step S304), the processing proceeds to step S305. In a case where the movement of the fundus does not occur (NO in step S304), the processing proceeds to step S308. In a case where the movement of the fundus is less than or equal to a predetermined threshold, the determination unit 101-32 may determine that the movement of the fundus does not occur.
<Step S305>

The determination unit 101-32 determines whether the amount of movement of the fundus calculated in step S303 is equal to or greater than a predetermined threshold. In the present exemplary embodiment, the determination unit 101-32 determines whether the amount of movement stored in the storage unit 101-02 is equal to or greater than the threshold. The threshold is a threshold for determining whether to perform rescanning.

In a case where the amount of movement is less than the threshold (NO in step S305), the determination unit 101-32 determines that, it is possible to continue scanning at the same part in the fundus by correcting the scanning position by tracking. Then, the processing proceeds to step S307. In a case where, on the other hand, the amount of movement is equal to or greater than the threshold (YES in step S305), the determination unit 101-32 determines that a tomographic image (a B-scan) requires rescanning (because the correction of the scanning position alone is insufficient). Then, the processing proceeds to step S306. In a case where it is determined that rescanning is required, the image capturing control unit 101-03 may discard signal data of tomographic images included in the cluster. The cluster that requires rescanning according to the determination may be discarded when the generation of tomographic images is completed in step S313. The discarding is the process of preventing the cluster from being used for the generation of a motion contrast image, and data or an image does not necessarily need to be erased from the storage unit 101-02. That is, the first generation unit 101-42 does not use, for the generation of the motion contrast image, the data set including the tomographic data that requires rescanning according to the determination.

In a case where the amount of movement is equal to or greater than the threshold (YES in step S305), then to rescan this part later, the determining unit 101-33 determines the B-scan number of a B-scan to be subjected to rescanning and stores the determined B-scan number in the storage unit 101-02. The determining unit 101-33 determines, as the B-scan number of the B-scan to be subjected to rescanning, identification information of the cluster including the B-scan image corresponding to the SLO image in which the amount of movement equal to or greater than the threshold is detected. Then, the determining unit 101-33 stores the identification information in the storage unit 101-02. For example, the determining unit 101-33 determines a cluster including a tomographic image acquired at approximately the same timing as the timing of acquisition of the SLO fundus image in which the amount of movement equal to or greater than the threshold is detected. The B-scan number may be identification information allowing the identification of a cluster including the B-scan, and the position in the fundus of the cluster. For example, the determining unit 101-33 can determine the B-scan number from control information of a scanner used when the cluster scanning is executed in step S302.

In a case where rescanning is required according to the determination, and the cluster to be subjected to rescanning is determined, the image capturing control unit 101-03 may discard signal data of tomographic images included in the cluster. The cluster that requires rescanning according to the determination may be discarded when the generation of tomographic images is completed in step S313, The discarding is the process of preventing the cluster from being used for the generation of a motion contrast image, and data or an image does not necessarily need to be erased from the storage unit 101-02. Further, if one or more clusters are already acquired at the same position, a motion contrast image can be generated from the one or more already acquired clusters. Thus, rescanning does not necessarily need to be performed. That is, in the present invention, rescanning is not an essential requirement.

<Step S307>

To continue scanning at the same part in the fundus, the instruction unit 101-34 instructs the OCT device 100 to move the XY-scanner 216 to a position obtained by offsetting the amount of movement of the fundus calculated in step S303 with respect to the previous scanning position. If the estimated amount of movement also includes the angle in the rotational direction, the rotational direction is also corrected.

In the capturing of an OCTA image, to avoid the influence of a change in the focus position or the interruption of a light beam by the pupil or eyelashes as much as possible, it is desirable that a time Δt required to scan a single cluster should be fixed and as short as possible. Further, in fundus tracking control, it takes a certain time to move the XY-scanner 216. Thus, in OCTA, it is not desirable to correct the scanning position in cluster scanning. In response, in the present exemplary embodiment, the number of times m of scanning per cluster is set to be small (m=3), and then, the scanning position is corrected between the respective times of cluster scanning. The number of times of scanning per cluster is not limited to three.

<Step S308>

The image capturing control unit 101-03 confirms whether the B-scan number of the B-scan to be subjected to rescanning is stored in the storage unit 101-02. In a case where the B-scan number is stored (YES in step S308), the processing proceeds to step S309. In a case where the B-scan number is not stored (NO in step S308), the processing proceeds to step S310. If rescanning is repeated many times, the image capturing time becomes long, and the burden on the subject increases. Thus, an upper limit may be placed on the number of times of rescanning. In this case, if the number of times of rescanning reaches the upper limit, and even if the B-scan number of the B-scan to be subjected to rescanning is stored in the storage unit 101-02, the processing proceeds to step S310.

<Step S309>

The image capturing control unit 101-03 sets the B-scan number of the B-scan to be subjected to rescanning in the storage unit 101-02, and the processing returns to step S302. In step S302, the instruction unit 101-34 reads the B-scan number from the storage unit 101-02 and instructs the OCT device 100 to perform cluster scanning corresponding to the B-scan number. Based on the instruction, the OCT device 100 executes cluster scanning again. That is, scanning is performed again in the cluster including the B-scan to be subjected to rescanning according to the determination. The image acquisition unit 101-01 acquires signal data obtained by this rescanning. That is, the image acquisition unit 101-01 corresponds to an example of a reacquisition unit configured to reacquire, by rescanning, only as many pieces of tomographic data included in the data set determined by the determining unit.

The image capturing parameters are already indicated in step S301, and therefore do not need to be indicated again. The configuration may be such that focus control or coherence gate control is performed simultaneously when the rescanning is performed. The configuration may be such that similarly, focus control or coherence gate control is also performed simultaneously when the scanning position is corrected in step S307.

Figure 6A:
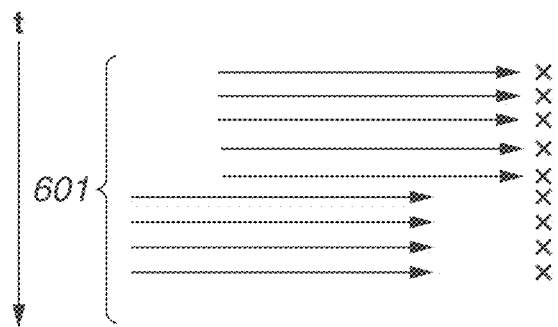
FIGS. 6A and 6B are diagrams illustrating examples of a rescanning process according to the present exemplary embodiment.
Figure 6B:
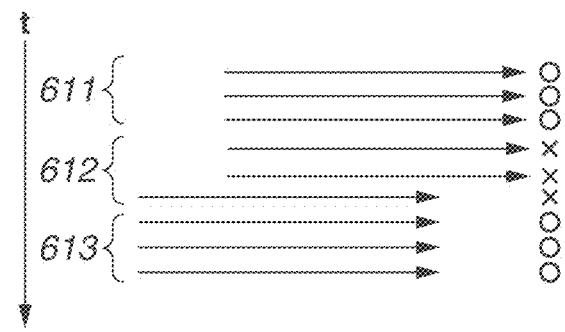

With reference to FIGS. 6A and 6B, examples of rescanning in the capturing of an OCTA image are described. In each of FIGS. 6A and 6B, the vertical axis represents the lapse of the image capturing time, and the horizontal axis represents the position in the main scanning direction. In the examples illustrated in FIGS. 6A and 6B, the movement of the subject's eye 200 equal to or greater than the threshold occurs between fifth and sixth B-scans. Further, in FIGS. 6A and 6B, a B-scan with "X" at its right end represents a B-scan as a rescanning target, and a B-scan with "Ω" represents a B-scan that, is not a rescanning target.

FIG. 6A represents B-scans in a case where cluster scanning is performed once according to m=9, as an example of the case where cluster scanning is performed once by setting the number of times of scanning per cluster to be great. That is, a cluster 601 includes nine B-scans. In the example illustrated in FIG. 6A, if the movement of the subject's eye 200 equal to or greater than the threshold occurs, all the (nine) B-scans included in the single cluster are set as rescanning targets.

On the other hand, in the example illustrated in FIG. 6B, similarly to FIG. 6A, B-scans are executed nine times, but the image capturing of clusters according to m=3 is repeated r=3 times. Thus, in FIG. 6B, three clusters 611 to 613 are illustrated. That is, FIG. 6B illustrates an example of cluster scanning performed by the flow illustrated in FIG. 3. Even if the movement of the subject's eye 200 equal to or greater than the threshold occurs between fifth and sixth B-scans similarly to FIG. 6A, only a B-scan group 612 (corresponding to three B-scans), which includes the sixth B-scan, needs to be set as a rescanning target. That is, in the present exemplary embodiment, even if B-scans are executed the same number of times, a plurality of B-scans are divided into a plurality of clusters, so that an increase in the image capturing time due to rescanning is suppressed, whereby the state of the subject's eye is made less unstable.

<Step S310>

The image capturing control unit 101-03 moves the XY-scanner 216 to the next scanning position. For example, the image capturing control unit 101-03 controls the XY-scanner 216 to perform scanning at a different position in the sub-scanning direction with measurement light.

<Step S311>

The image capturing control unit 101-03 determines whether the number of times of execution of cluster scanning at the same position in the fundus reaches a predetermined number of times r. In a case where the number of times of execution of cluster scanning reaches r (YES in step S311), the processing proceeds to step S312. In a case where the number of times of execution of cluster scanning does not reach r (NO in step S311), then after the lapse of a predetermined time allowing the subject to blink, the processing proceeds to step S302. During the waiting time while the processing proceeds to step S302, a mark or characters (having a predetermined color or shape) indicating that the subject is allowed to blink at the current time may be displayed on the display unit 104. Further, the provision of the time allowing the subject to blink is not an essential process in the present invention. Thus, the processing may immediately proceed to step S302. Further, in the present exemplary embodiment, step S311 is executed after step S310, whereby cluster scanning is performed once at each position in the sub-scanning direction, and then, cluster scanning is performed again at each position in the sub-scanning direction. However, step S310 may be executed after step S311, whereby cluster scanning may be executed r times at a single positron in the sub-scanning direction, and then, cluster scanning may be executed r times at a next predetermined position in the sub-scanning direction.

<Step S312>

The image capturing control unit 101-03 determines whether all the B-scans are completed. In a case where there is a B-scan that is not completed, the control of the information processing apparatus 101 returns to step S302.

<Step S313>

The tomographic image generation unit 101-11 reconfigures signal data of tomographic images acquired by the image acquisition unit 101-01 to generate tomographic images. The tomographic images may be generated before step S312 at any timing after step S302.

Further, the image processing unit 101-04 performs registration between the generated tomographic images to acquire layer boundary data. Further, the image processing unit 101-04 calculates a motion contrast value between tomographic images temporally adjacent to each other to generate a motion contrast image.

Further, the image processing unit 101-04 saves in the storage unit 102 the tomographic images or the motion contrast data acquired in steps S302 to S312 in association with the examination date and time or information identifying the subject's eye 200.

With reference to a flowchart illustrated in FIG. 7B, the details of interference signal processing executed in step S313 are described. FIG. 7B is a flowchart illustrating an example of the detailed process of step S313.

The image processing unit 101-04 starts signal processing in a k-th (k=1, 2, . . . , r) cluster at a scanning position yi in the sub-scanning direction (the Y-axis direction).

<Step S313-02>

The image processing unit 101-04 starts signal processing at the scanning position yi (i=1, 2, . . . , n−1, n) in the Y-axis direction.

If rescanning data (data acquired by rescanning) corresponding to the number of times k of cluster scanning and the Y-position yi is present, the process of reconfiguring tomographic data is performed on only the data acquired by the rescanning.

<Step S313-03>

The image processing unit 101-04 starts signal processing on a j-th (j=1, 2, . . . , m) B-scan image belonging to the k-th cluster at the scanning position yi in the Y-axis direction.

<Step S313-04>

The tomographic image generation unit 101-11 generates a tomographic image. Specifically, the tomographic image generation unit 101-11 removes fixed noise from interference signal data. Next, the tomographic image generation unit 101-11 performs spectral shaping and dispersion compensation on the interference signal data and calculates the absolute value of a complex signal obtained by performing discrete Fourier transform on the signal data, to obtain intensity data regarding depth. For example, the tomographic image generation unit 101-11 performs the process of clipping any area from the intensity data to generate a tomographic image. The process of step S313-04 may be executed before step S312 at any timing after step S302.

The configuration may be such that based on the luminance value of the generated tomographic image, the determination unit 101-32 determines whether the acquisition of tomographic data is successful or failed. Based on any known indicator, it may be determined whether the acquisition of tomographic data is failed. In the present exemplary embodiment, if the signal-to-noise (S/N) ratio of the tomographic image is less than a predetermined value, it is determined that the acquisition of tomographic data is failed. The present invention is not limited to this. Alternatively, if at least one of the average value, the contrast, and the standard deviation of the histogram of the tomographic image is less than a predetermined value, it may be determined that the acquisition of tomographic data is failed. That is, the determination unit 101-32 corresponds to an example of a determination unit configured to determine whether acquisition of the tomographic data is successful or failed. If tomographic data of which the acquisition is failed according to the determination by the determination unit 101-32 occurs, the determining unit 101-33 determines as a rescanning target a cluster including the tomographic data of which the acquisition is failed. The OCT device 100 does not necessarily need to perform rescanning. Alternatively, a motion contrast image may be generated based on already acquired clusters.

<Step S313-05>

The image processing unit 101-04 determines whether the number of times of repetition of signal processing in the k-th cluster at the position yi in the Y-axis direction reaches a predetermined, number (m). That is, the image processing unit 101-04 determines whether the reconfiguration of an image at the position yi is repeated m times. In a case where the number of times of the reconfiguration of an image at the position yi does not reach the predetermined number (m), the processing returns to step S313-03. In step S313-03, the reconfiguration of an image at the same Y-position is repeated. In a case where the number of times of the reconfiguration of an image at the position yi reaches the predetermined number (m), the processing proceeds to step S313-06.

<Step S313-06>

The registration unit 101-41 performs registration between m B-scans belonging to the k-th cluster at the certain position yi. Specifically, the registration unit 101-41 selects any one of the m B-scans as a reference image and performs registration between the selected B-scan image and the other (m−1) B-scan images. As the registration method, for example, an evaluation function indicating the degree of similarity between images is defined in advance, and the registration unit 101-41 transforms images so that the value of the evaluation function is the best. In the present exemplary embodiment, a correlation coefficient is used as the evaluation function. The present invention is not limited to this. Alternatively, any known indicator of the degree of similarity or the degree of difference may be used as the evaluation function. Further, in the present exemplary embodiment, an affine transformation is used as the process of transforming images. The present invention, however, is not limited to this. Alternatively, registration may be performed using any known registration technique.

<Step S313-07>

The image feature acquisition unit 101-44 acquires layer boundary data of the fundus using at least one of the tomographic images in the clusters. In the present exemplary embodiment, the process of detecting layer boundary data based on a variable shape model is performed on a superimposed image obtained by averaging m tomographic images. The present invention is not limited to this. Alternatively, for example, the image feature acquisition unit 101-44 may select representative images from the clusters and detect layer boundaries from the representative images. Each representative image is, for example, a tomographic image captured in a predetermined frame, or a tomographic image having the highest contrast. Further, the method for detecting the layer boundary data is not limited to the variable shape model. Alternatively, any known segmentation technique may be used.

In a case where a motion contrast image is generated only in three dimensions, and a two-dimensional motion contrast image projected in the depth direction is not generated, this step may be omitted.

<Step S313-03>

The first generation unit 101-42 calculates one or more motion contrast values using the m B-scans belonging to the k-th cluster at the position yi in the Y-axis direction. The first generation unit 101-42 calculates motion contrast values to generate motion contrast images. In the present exemplary embodiment, the first generation unit 101-42 calculates decorrelation values at each pixel position between the m tomographic images ((m−1) sets) and generates (m−1) motion contrast images using the decorrelation values as motion contrast values. Further, the first generation unit 101-42 averages the (m−1) motion contrast images to generate a single motion contrast image per cluster. The motion contrast images may not be averaged in this step, and may be averaged in step S313-11. That is, at least one motion contrast image per cluster is obtained in this step.

As the indicator used to calculate motion contrast, any known indicator may be calculated so long as the indicator indicates changes over time in the luminance values at each pixel position of the B-scan images belonging to the cluster. Further, a statistic to be calculated to generate a single motion contrast image from the (m−1) motion contrast images is not limited to an average value. Alternatively, for example, any known statistic such as a median may be selected.

Further, the configuration may be such that the evaluation unit 101-421 determines whether a tomographic image inappropriate for generating a motion contrast image is included, and if a tomographic image inappropriate for generating a motion contrast image is included, a motion contrast image is not generated using this tomographic image. For example, the evaluation unit 101-421 calculates an evaluation value (e.g., a decorrelation value) limited to a retinal inner layer area, using the layer boundary acquired in step S313-07, and if the evaluation value is outside a predetermined range, the evaluation unit 101-421 determines that a tomographic image inappropriate for generating a motion contrast image is included.

If the cluster includes t tomographic images inappropriate for generating a motion contrast image, (m−t−1) motion contrast images are generated in this step. Then, the first generation unit 101-42 averages the (m−t−1) motion contrast images to generate a single motion contrast image per cluster. Further, the evaluation unit 101-421 may discard the cluster including the tomographic image inappropriate for generating a motion contrast image according to the determination based on the decorrelation value.

In this step, the first generation unit 101-42 generates a motion contrast image from a data set not including the tomographic data that requires rescanning according to the determination by the determination unit, and also generates a motion contrast image from a data set including tomographic data acquired by the rescanning.

<Step S313-09>

The image processing unit 101-04 determines whether the process of averaging the motion contrast data in the cluster at the position yi in the Y-axis direction is executed up to a position yn. In a case where the y-position where the process of averaging the motion contrast data in the cluster is completed does not reach yn, the processing returns to step S313-02. In a case where the y-position reaches yn, the processing proceeds to step S313-10.

<Step S313-10>

The image processing unit 101-04 determines whether the signal processing in the k-th cluster at the position yi in the Y-axis direction is repeated r times. In a case where the number of times of repetition does not reach a predetermined number (r), the processing returns to step S313-01. In a case where the number of times of repetition reaches the predetermined number (r), the processing proceeds to step S313-11. The image processing unit 101-04 generates a motion contrast image once at each position in the sub-scanning direction and then generates a motion contrast image at each position in the sub-scanning direction again. The present invention, however, is not limited to this. For example, the image processing unit 101-04 may generate motion contrast images for all the clusters at each position in the sub-scanning direction and then generate motion contrast images at the next position in the sub-scanning direction.

<Step S313-11>

The second generation unit 101-43 combines a plurality of motion contrast images obtained from a plurality of clusters at each y-position. For example, if three clusters are present, the second generation unit 101-43 combines three motion contrast images obtained from the respective clusters. That is, the second generation unit 101-43 combines the plurality of motion contrast images generated by the first generation unit 101-42 to generate the single motion contrast image.

More specifically, the second generation unit 101-43 performs registration between the motion contrast images and then generates an image having the average value of the motion contrast values at each pixel position. As the registration technique, any known registration technique may be applied. Further, in the present exemplary embodiment, an average value is used as the method, for combining motion contrast values at each pixel position. The present invention, however, is not limited to this. Alternatively, any known combination method such as a median may be used. If the plurality of motion contrast images obtained from the single cluster in step S313-08 are not averaged, the second generation unit 101-43 combines three or more motion contrast images obtained from three clusters. Further, the second generation unit 101-43 may combine only a plurality of motion contrast images generated from clusters other than the cluster including the tomographic data of which the acquisition is failed according to the determination by the determination unit 101-32.

At each y-position, a motion contrast image at a predetermined position in the fundus is obtained. Thus, when this step ends, a three-dimensional motion contrast image (corresponding to the lumen area of blood vessels in three dimensions) is obtained.

<Step S313-12>

The projection unit 101-45 identifies the projection range in the depth direction based on the layer boundary data acquired in step S313-07 and then projects, in the depth direction, three-dimensional data regarding the motion contrast values generated in step S313-11, to generate a two-dimensional motion contrast image (an en-face image). In the present exemplary embodiment, maximum value projection is used as the projection method. The prevent invention, however, is not limited to this. Alternatively, any known projection method may be used. If an en-face image is not necessary, this step may be omitted.

<Step S313-13>

The image processing unit 101-04 saves in the storage unit 102 the tomographic images or the motion contrast image acquired in steps S302 to S312 in association with the examination date and time or information identifying the subject's eye 200.

<Step S314>

Referring back to FIG. 3, in step S314, the display control unit 101-05 causes the display unit 104 to display at least one of the tomographic images and the motion contrast image generated in step S313. The motion contrast image to be displayed may be an en-face image or a three-dimensional image.

In the present exemplary embodiment, as described above, the number of tomographic images included in a single cluster is smaller than that in a conventional method. That is, the number of times of scanning in a single cluster is smaller than that in the conventional method. Then, a motion contrast image is generated with respect to each cluster, and ultimately, a plurality of motion contrast images are combined together to generate a motion contrast image to be displayed.

Thus, according to the present exemplary embodiment, the eye is easily stabilized in a single cluster. Thus, it is less likely that all tomographic images included in the cluster are discarded. Thus, according to the present exemplary embodiment, it is possible to stably acquire a motion contrast image.

Further, according to the present exemplary embodiment, the eye is easily stabilized in a single cluster. Thus, it is possible to reduce the occurrence frequency of rescanning. Further, even in a case where rescanning is performed, the number of tomographic images in a single cluster is smaller than that in the conventional method. Thus, it is possible to reduce the scanning time to be spent on the rescanning. That is, in the conventional method, the time until a motion contrast image is obtained by rescanning is prolonged. According to the present exemplary embodiment, however, even in a case where rescanning is performed, it is possible to reduce the above prolonged time.

For example, in the examples illustrated in FIGS. 6A and 6B, in the conventional method, nine tomographic images are included in a single cluster, and eight motion contrast images are generated. On the other hand, in the method according to the present exemplary embodiment, nine tomographic images are divided into three clusters. Then, two motion contrast images are generated from each of the three clusters. Thus, a total of six motion contrast images are generated. That is, the number of motion contrast images generated in the present exemplary embodiment is smaller than that in the conventional method. According to the present exemplary embodiment, however, since the number of tomographic images included in a cluster is smaller, the eye is easily stabilized. Thus, it is possible to stably acquire a motion contrast image. Further, according to the present exemplary embodiment, the number of tomographic images in a single cluster is also six images less than that in the conventional method. Thus, it takes less time to perform rescanning. Further, according to the present exemplary embodiment, even in a case where some of the clusters need to be discarded due to the motion of the eye, a motion contrast image can be generated from the other clusters. Thus, it is possible to reduce the possibility that if the subject's eye 200 is not stabilized, a motion contrast image cannot be acquired for a long time as in the conventional method.

(Variation 1)

In the above exemplary embodiment, a case has been described where cluster scanning is performed multiple (r) times at the same position in the fundus. The present invention, however, is not limited to this.

Figure 5B:
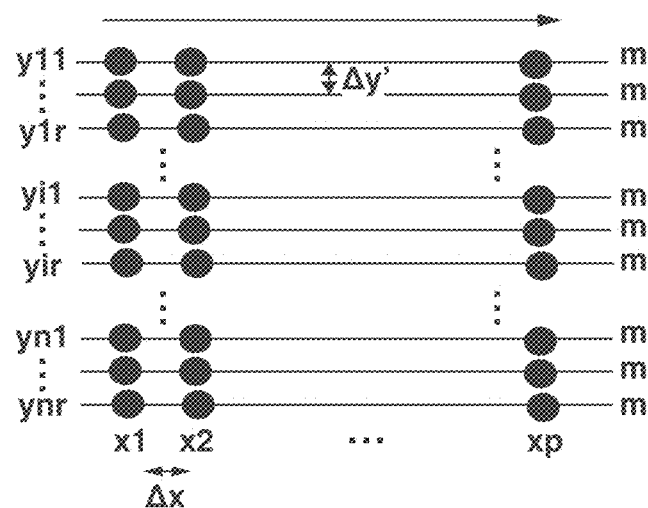

For example, as illustrated in FIG. 5B, each of the positions of cluster scanning to be performed multiple (r) times may be shifted by $\Delta y'$ ($\Delta y' < \Delta y$) in the sub-scanning direction (from yil to yir), and an image may be captured. For example, in a case where cluster scanning is performed three times (r=3) such that $\Delta y=10$ µm, an OCTA image may be captured such that $\Delta y'=3$ µm.

Figure 5C:
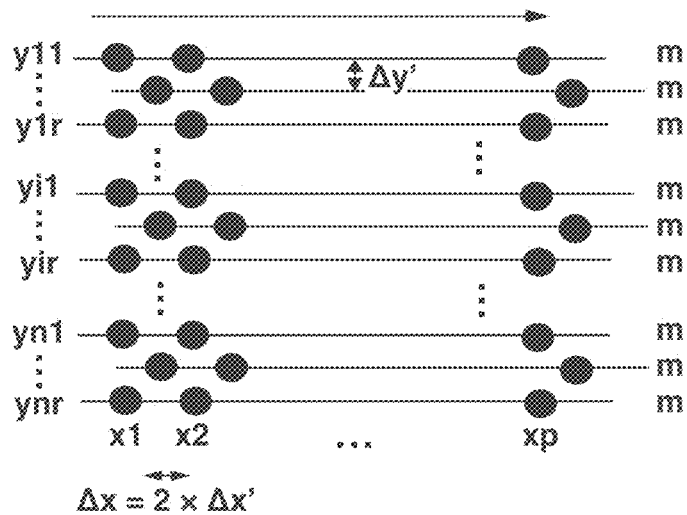

Alternatively, as illustrated in FIG. 5C, each of the positions of cluster scanning may be alternately shifted by $\pm\Delta x'$ ($|\Delta x'| < \Delta x$) in the main, scanning direction (from yil to yir), and an image may be captured. For example, in a case where cluster scanning is performed three times (r=3) such that $\Delta x=10$ µm, an OCTA image may be captured such that $|\Delta x'|=5$ µm. The numerical values of $\Delta y$ and $\Delta x$ are illustrative, and therefore may be other numerical values. Further, the positions of cluster scanning may be changed in the main scanning direction and the sub-scanning direction. That is, in this variation, pieces of tomographic data included in different data sets from among the plurality of clusters (data sets) are pieces of tomographic data obtained based on measurement light controlled to perform scanning at different positions in at least either one of an X-direction and a Y-direction on an XY-plane orthogonal to a depth direction of the section of the fundus.

In this manner, it is possible to acquire a higher-quality motion contrast image.

(Variation 2)

In the above exemplary embodiment, an example has been described where in a case where rescanning is performed, the process of reconfiguring signal data that requires rescanning according to a determination is not performed, and the process of reconfiguring only signal data obtained by rescanning is performed. The present invention, however, is not limited to this.

For example, the configuration may be such that the process of reconfiguring signal data that requires rescanning according to a determination is performed, but the motion contrast value of the signal data that requires rescanning according to the determination is not calculated in step S313-08. Alternatively, the configuration may be such that the process of reconfiguring signal data that requires rescanning according to a determination is performed, and the motion contrast value of the signal data is calculated, but the combining process in step S313-11 is not performed using the signal data.

Second Exemplary Embodiment

In the first exemplary embodiment, an example has been described where cluster scanning is executed multiple times at each position in the sub-scanning direction. In a second exemplary embodiment, an example is described where an information processing apparatus according to the present exemplary embodiment changes, with respect to each area in an eye portion, the number of times of cluster scanning to be executed at the same position. Cluster scanning is executed more times only in a necessary area than in another area, whereby it is possible to reduce unnecessary cluster scanning while acquiring a high-contrast motion contrast image regarding the necessary area. Further, since unnecessary cluster scanning is not performed, it is possible to reduce the possibility that the eye is not stabilized. Thus, it is possible to stably acquire a motion contrast image.

In the present exemplary embodiment, for example, the OCT device 100 executes predetermined cluster scanning in a first area including a macular portion and an optic disc portion and then performs additional cluster scanning in a second area (a macular portion including the fovea) where the contrast is likely to decrease. For example, the second area is smaller than the first area. The information processing apparatus 101 combines a motion contrast image obtained by performing the cluster scanning in the first area and a motion contrast image obtained by performing the cluster scanning in the second area. By this combining process, a high-contrast motion contrast image is generated.

The details of the present exemplary embodiment are described below.

The configuration of the information processing system 10 including the information processing apparatus 101 according to the present exemplary embodiment is similar to that according to the first exemplary embodiment, and therefore is not described here. Further, FIG. 8A is a flowchart illustrating an example of image processing according to the present exemplary embodiment. Steps other than steps S801, S802, S811, and S813 are similar to the first exemplary embodiment, and therefore are not described here. Steps S801 to S814 correspond to steps S301 to S314.
<Step S801>
The image feature acquisition unit 101-44 detects, from an image of an eye portion acquired by the image acquisition unit 101-11, an image feature of the eye portion and changes image capturing conditions (weights image capturing parameters) with respect to each area in the fundus. The specific processes of detecting the image feature and weighting the image capturing parameters will be described with reference to steps S801-01 to S801-03 illustrated in FIG. 8B.

<Step S801-01>
The image acquisition unit 101-01 acquires from the OCT device 100 an image of an eye portion necessary to acquire an image feature of the subject's eye 200. In the present exemplary embodiment, the image acquisition unit 101-01 acquires an SLO fundus image as the image of the eye portion. The image acquisition unit 101-01 may acquire not only an SLO fundus image but also, for example, a tomographic image of the eye portion.
<Step S801-02>
The image feature acquisition unit 101-44 acquires an image feature of the eye portion from the image acquired in step S801-01. In the present exemplary embodiment, the image feature acquisition unit 101-44 acquires at least one of, for example, the fovea, the retinal vascular arcades, and the optic disc area as the image feature of the eye portion from the SLO fundus image acquired in step S801-01. Further, the image feature acquisition unit 101-44 may acquire retinal arteriovenous crossings from the SLO fundus image. As the method for acquiring the image feature of the eye portion, any known image processing technique may be used. For example, the retinal vascular arcades can be acquired by using any known line emphasis filter on the SLO fundus image.

The image feature acquisition unit 101-44 may acquire a predetermined part (the fovea or the optic disc) or a layer boundary forming the retina or the choroid from not only the SLO fundus image but also, for example, a tomographic image obtained by prescanning. The image feature acquisition unit 101-44 can detect the fovea or the optic disc portion using any known image processing technique. For example, the image feature acquisition unit 101-44 acquires the internal limiting membrane (ILM) using a variable shape model from a tomographic image, and based on the position in the depth direction of the ILM, identifies two depressed portions in depth order. Then, the image feature acquisition unit 101-44 determines the deepest depressed portion in the depth direction as the optic disc portion and determines the second deepest depressed portion in the depth direction as the fovea. Further, the image feature acquisition unit 101-44 can acquire the layer boundary using any known segmentation process such as a variable shape model as the method for acquiring the layer boundary.
<Step S801-03>
Based on the image feature of the eye portion acquired in step S801-02, the determining unit 101-33 determines an additional scanning method (a target area of additional scanning and the number of times of scanning in the additional scanning).

First, examples of the target area of the additional scanning include the following (i) to (iii).
(i) Common Site for Lesion
Examples of a common site for a lesion include the boundary of the foveal avascular zone (FAZ), the retinal outer layer under the fovea, the choroid, a retinal arteriovenous crossing portion, and an optic disc portion. Further, examples of a lesion include a capillary blockage and a microaneurysm.
(ii) Area Where Fundus Shape Satisfies Predetermined Condition
Examples of an area where the fundus shape satisfies a predetermined condition include an area where the thickness of a layer forming the retina or the choroid is outside a predetermined range. For example, a part where the thickness of a predetermined layer of the fundus is less than a normal value may be an area where the fundus shape satisfies the predetermined condition.

(iii) Area Where Acquired Motion Contrast Data Satisfies Predetermined Condition This area is, for example, an area where an indicator value (the contrast or the vascular density) calculated for motion contrast data generated from tomographic images obtained by the first cluster scanning is outside the range of acceptable values.

Next, the method for determining the number of times of scanning in the additional scanning (the number of times m of scanning per cluster) is described. For example, the number of times of scanning in the additional scanning is determined as follows. In this case, the default value of r regarding the additional cluster scanning is 1, but may be r≥2.

m=((the number of pieces of motion contrast data to be acquired at the same position)−(the number of pieces of motion contrast data acquired by the first cluster scanning))/r+1 m and r regarding the additional scanning are merely illustrative, and may be other values. For example, the value of the number of times (m) of scanning may be different between the respective times of cluster scanning.

Figure 4A:
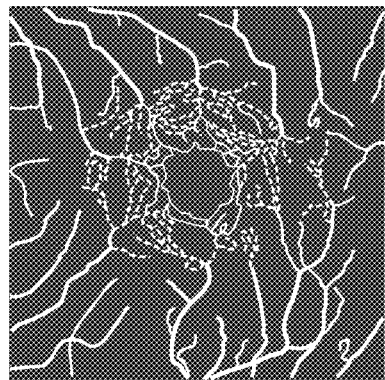
FIGS. 4A, 4B, and 4C are diagrams illustrating examples of optical coherence tomography angiography (OCTA) images.
Figure 4B:
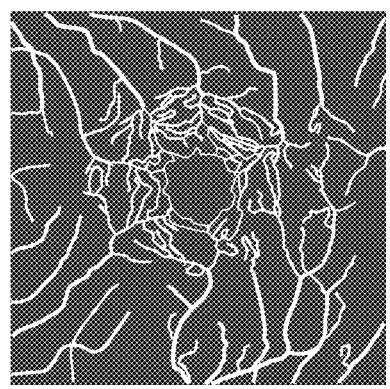
Figure 4C:
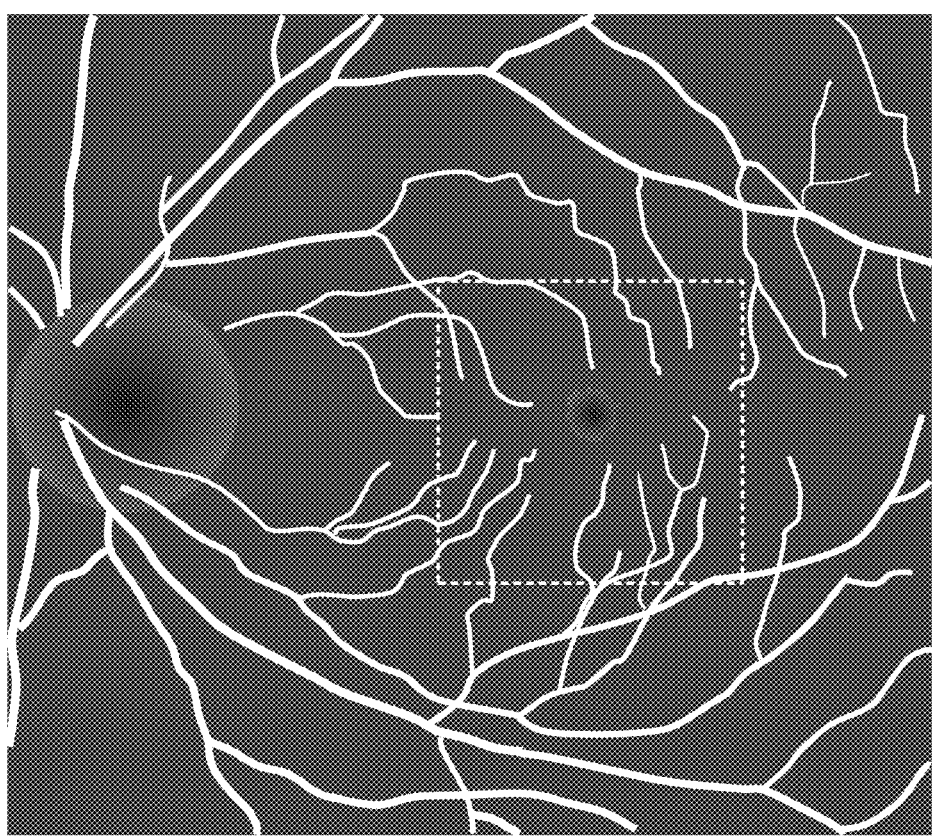

In the present exemplary embodiment, cluster scanning is performed in, for example, an area of 3 mm×3 mm including the fovea as indicated by a dotted line portion in FIG. 4C. As examples, the number of times of scanning in additional cluster scanning is set to m=3, and the number of times of cluster scanning is set to r=1.

In a case where additional cluster scanning is performed as described above, the area of the entirety of the fundus illustrated in FIG. 4C is scanned according to m=3. Thus, four motion contrast images are acquired regarding the area, of the dotted line portion in FIG. 4C, That is, it is possible to acquire motion contrast images corresponding to a case where the number of times of scanning in cluster scanning is five.

Thus, according to the present exemplary embodiment, cluster scanning according to m=5 is performed in a diagnostically important area including a common site for a lesion. Then, a high-contrast motion contrast image is acquired based on four pieces of motion contrast data. That is, the information processing apparatus 101 according to the present exemplary embodiment can acquire more motion contrast images regarding a partial area than another area in the fundus.

The present invention is not limited to this. Alternatively, any area can be specified so long as the OCT device 100 can capture this area as a target area of additional scanning. That is, a target area of additional scanning may be automatically determined by analyzing an image, or may be determined by the user.

Further, a plurality of target areas of additional scanning may be set, and with respect to each target area of the additional scanning, at least one of the number of times m of scanning in cluster scanning and the number of times r of cluster scanning may be determined to be different.

<Step S802>

Based on the image capturing conditions indicated in step S801, the image capturing control unit 101-03 causes the OCT device 100 to execute cluster scanning, i.e., repeat B-scans m times at the same position in the fundus. In the present exemplary embodiment, as a target area of the first cluster scanning in this step, an area of 10 mm×10 mm including an optic disc portion and a macular portion as illustrated in FIG. 4C is set. Thus, the OCT device 100 performs cluster scanning in the area of 10 mm×10 mm according to m=3.

In the second cluster scanning, the area of 3 mm×3 mm including the fovea as indicated by the dotted line portion in FIG. 4C is set as a target area of cluster scanning. Thus, the OCT device 100 performs cluster scanning in the area of 3 mm×3 mm according to m=3.

The image capturing control unit 101-03 determines whether the number of times of execution of cluster scanning at approximately the same position reaches a predetermined number of times (r). In the present exemplary embodiment, the predetermined number of times is set to r=2 only for the area of 3 mm×3 mm including the fovea. In a case where the number of times of execution of the cluster scanning reaches the predetermined number of times (r) (YES in step S811), the processing proceeds to step S812. In a case where the number of times of execution of the cluster scanning does not reach the predetermined number of times (r) (NO in step S811), the processing proceeds to step S802 so that the OCT device 100 performs additional scanning. After performing cluster scanning in the area of 10 mm×10 mm once, the OCT device 100 may perform, cluster scanning in the area of 3 mm×3 mm. The present invention, however, is not limited to this. For example, while cluster scanning is performed in the area of 10 mm×10 mm, and when the scanning in the sub-scanning direction reaches the area of 3 mm×3 mm, the OCT device 100 may perform the second cluster scanning in the area of 3 mm×3 mm.

<Step S813>

Although the process of step S813 is basically similar to the process of step S313, processing different from that in the first exemplary embodiment is described with reference to FIG. 7B.

The portions represented as "step S313-" in FIG. 7B are replaced with "step S813-". Processes other than that of step S813-11 are similar to the first exemplary embodiment, and therefore, only the process of step S813-11 is described.

<Step S813-11>

The second generation unit 101-43 combines pieces of motion contrast data generated by the first generation unit 101-42. Specifically, the second generation unit 101-43 performs registration between pieces of motion contrast data generated by the first generation unit 101-42 and then generates an image having the average value of the motion contrast values at each pixel position. Similarly to step S313-11, a median may be used instead of the average value.

In the present exemplary embodiment, the number of times of cluster scanning is set to r=2, and a motion contrast image having a wide angle of view as illustrated in FIG. 4C and a motion contrast image having a small angle of view as illustrated in FIG. 4A obtained by additional cluster scanning are obtained. Thus, the second generation unit 101-43 combines both motion contrast images to generate a high-contrast OCTA image having a wide angle of view, in which the definition of capillary blood vessels is high also near the fovea as illustrated in FIG. 4B. That is, a motion contrast image of the area of 3 mm×3 mm including the fovea has higher contrast than a motion contrast image of another area. Although the capillary blood vessels are not illustrated in FIG. 4C, actually, the capillary blood vessels are also visualized.

In the present exemplary embodiment, a case has been described where images are captured by fixing the number of times of additional scanning. The present invention, however, is not limited to this. For example, the configuration may be such that when motion contrast images generated by the first generation unit 101-42 are combined together, the evaluation unit 101-421 evaluates a predetermined indicator value (e.g., the contrast or the vascular density) of each motion contrast image. If the indicator value is not within a predetermined range, the information processing apparatus 101 causes the OCT device 100 to perform additional scanning until the indicator value falls within the predetermined range. Then, the second generation unit 101-43 combines pieces of motion contrast data also including motion contrast data obtained by the additional scanning.

Also with the above configuration, it is possible to achieve effects similar to those of the first exemplary embodiment. Further, according to the present exemplary embodiment, a motion contrast image is generated by changing the number of times of cluster scanning with respect to each area in an eye portion, whereby it is possible to acquire a high-contrast motion contrast image more stably.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-006977, filed Jan. 18, 2017, which is hereby incorporated by reference herein in its entirety.

What is claimed is:

1. An information processing apparatus comprising:
a memory storing a program; and
one or more processors which, by executing the program, function as:
an obtaining unit configured to obtain data sets each of which includes a plurality of pieces of tomographic data that represents a section of an eye and obtained based on measurement light controlled to perform scanning at the same position in the eye in the same direction, the data sets not including the same tomographic data as each other;
a first generation unit configured to generate motion contrast images corresponding to the data sets by generating at least one motion contrast image from each of the data sets, without generating a motion contrast image from across the data sets, wherein the at least one motion contrast image represents a cross section in a depth direction of the eye;
a second generation unit configured to generate a single three-dimensional motion contrast image using three-dimensional motion contrast images corresponding to the generated motion contrast images; and
a third generation unit configured to identify, using information about a layer boundary obtained by using at least one piece of tomographic data among the plurality of pieces of tomographic data included in the data set, a partial region of the single three-dimensional motion contrast image in the depth direction of the eye, and to generate a motion contrast en-face image corresponding to the identified partial region.

2. The information processing apparatus according to claim 1, further comprising:
a determination unit configured to determine tomographic data that requires rescanning;
a determining unit configured to determine, from among the data sets, a data set including the tomographic data that requires rescanning according to the determination by the determination unit; and
a reacquisition unit configured to reacquire, by rescanning, only as many pieces of tomographic data included in the data set determined by the determining unit.

3. The information processing apparatus according to claim 1, further comprising:
a determination unit configured to determine whether acquisition of the tomographic data is successful or failed; and
a determining unit configured to determine a data set including the tomographic data of which the acquisition is failed according to the determination by the determination unit,
wherein, using a motion contrast image obtained from, among the data sets, a data set other than the data set determined by the determining unit, the second generation unit generates the single motion contrast image representing the cross section.

4. The information processing apparatus according to claim 1, wherein each of the plurality of pieces of tomographic data included in the data sets is tomographic data representing a section of the eye and obtained using the measurement light controlled to perform scanning at the same position.

5. The information processing apparatus according to claim 1, wherein pieces of tomographic data included in different data sets among the data sets are pieces of tomographic data obtained using measurement light controlled to perform scanning at different positions in at least either one of an X-direction and a Y-direction on an XY-plane orthogonal to a depth direction of the eye.

6. The information processing apparatus according to claim 1, wherein the numbers of pieces of tomographic data included in the data sets are equal to each other.

7. The information processing apparatus according to claim 1, wherein the numbers of pieces of tomographic data included in the data sets are two or three.

8. The information processing apparatus according to claim 2,
wherein the first generation unit generates a motion contrast image from a data set not including the tomographic data that requires rescanning according to the determination by the determination unit, and also generates a motion contrast image from a data set including tomographic data acquired by the rescanning, and wherein the second generation unit combines the plurality of motion contrast images generated by the first generation unit to generate the single motion contrast image.

9. The information processing apparatus according to claim 8, wherein the first generation unit does not use, for the generation of the motion contrast image, the data set including the tomographic data that requires rescanning according to the determination.

10. The information processing apparatus according to claim 1, wherein the second generation unit combines the plurality of motion contrast images obtained from the plurality of respective data sets to generate the single motion contrast image representing the cross section.

11. An information processing method comprising:
obtaining data sets, each data set including a plurality of pieces of tomographic data that represents a section of an eye and obtained using measurement light controlled to perform a plurality of scans at the same position in the eye in the same direction a plurality of times, the data sets not including the same tomographic data as each other;
generating motion contrast images corresponding to the data sets by generating at least one motion contrast image from each of the data sets, without generating a motion contrast image from across the data sets, wherein the at least one motion contrast image represents a cross section in a depth direction of the eye;
generating a single three-dimensional motion contrast image using three-dimensional motion contrast images corresponding to the generated motion contrast images; and
identifying, using information about a layer boundary obtained by using at least one piece of tomographic data among the plurality of pieces of tomographic data included in the data set, a partial region of the single three-dimensional motion contrast image in the depth direction of the eye, and generating a motion contrast en-face image corresponding to the identified partial region.

12. A non-transitory storage medium having stored therein a program for causing a computer to execute:
obtaining data sets, each data set including a plurality of pieces of tomographic data that represents a section of an eye and obtained using measurement light controlled to perform a plurality of scans at the same position in the eye in the same direction a plurality of times, and the data sets not including the same tomographic data as each other;
generating motion contrast images corresponding to the data sets by generating at least one motion contrast image from each of the data sets, without generating a motion contrast image from across the data sets, wherein the at least one motion contrast image represents a cross section in a depth direction of the eye;
generating a single three-dimensional motion contrast image using three-dimensional motion contrast images corresponding to the generated motion contrast images; and
identifying, using information about a layer boundary obtained by using at least one piece of tomographic data among the plurality of pieces of tomographic data included in the data set, a partial region of the single three-dimensional motion contrast image in the depth direction of the eye, and generating a motion contrast en-face image corresponding to the identified partial region.

13. The information processing apparatus according to claim 1, wherein the single motion contrast image has an average value of motion contrast.

14. The information processing apparatus according to claim 1, further comprising an image capturing control unit configured to control an OCT device to perform cluster scannings using an image capturing condition set by instruction from an operator, the each data set being obtained by performing each cluster scanning.

15. The information processing apparatus according to claim 14, further comprising a movement amount calculation unit configured to calculate a movement amount using funds images obtained at different times,
wherein the image capturing control unit controls the measurement light using the calculated movement amount so as to correct a scanning position between one cluster scanning and a next cluster scanning.

16. The information processing apparatus according to claim 1, further comprising an acquisition unit configured to acquire the information about the layer boundary using a superimposed image acquired by using the plurality of pieces of tomographic data included in the data set.

17. The information processing apparatus according to claim 1, further comprising an acquisition unit configured to acquire the information about the layer boundary using a tomographic image selected as a representative image, the representative image corresponding to any of the plurality of pieces of tomographic data included in the data set.

18. The information processing apparatus according to claim 1, further comprising a determination unit configured to determine a partial region of a first region of the eye as a second region to be additionally scanned, the partial image corresponding to the three-dimensional motion contrast image.

19. The information processing apparatus according to claim 1, wherein the three-dimensional motion contrast images are generated by using data sets obtained by acquiring, as a single cluster, a single data set at a position in a direction intersecting with the same direction and data sets obtained by re-acquiring, as a single cluster, a single data set at a position in the direction intersecting with the same direction.

* * * * *